(12) United States Patent
Xu et al.

(10) Patent No.: US 6,341,532 B1
(45) Date of Patent: Jan. 29, 2002

(54) SHEAR FORCE MICROSENSOR

(75) Inventors: Diao Xu; Teng Yong Ng; Tieying Jiang; Khin Yong Lam; Boo Cheong Khoo, all of Singapore (SG)

(73) Assignee: Institute of High Performance Computing, Singapore (SG)

(*) Notice: Subject to any disclaimer, the term of this patent is extended or adjusted under 35 U.S.C. 154(b) by 0 days.

(21) Appl. No.: 09/667,511

(22) Filed: Sep. 22, 2000

(30) Foreign Application Priority Data

Nov. 19, 1999 (SG) ............................................. 9905851

(51) Int. Cl.$^7$ ................................................ G01N 3/24
(52) U.S. Cl. ........................................... 73/841; 73/147
(58) Field of Search ........................ 73/147, 841, 842, 73/774, 777, 780

(56) References Cited

U.S. PATENT DOCUMENTS

| | | | |
|---|---|---|---|
| 4,464,928 A | | 8/1984 | Dealy |
| 4,879,899 A | * | 11/1989 | Leehey ........................ 73/147 |
| 4,896,098 A | * | 1/1990 | Haritonidis et al. ......... 324/663 |
| 5,052,228 A | * | 10/1991 | Haritonidis ................... 73/705 |
| 5,199,298 A | * | 4/1993 | Ng et al. ....................... 73/147 |
| 5,623,096 A | * | 4/1997 | Bandyopadhyay ............ 73/147 |

FOREIGN PATENT DOCUMENTS

DE 33 33 920 A1 4/1984

* cited by examiner

*Primary Examiner*—Max Noori
(74) *Attorney, Agent, or Firm*—Nixon & Vanderhye P.C.

(57) ABSTRACT

A micro-dimensional sensor measures the shear force, both in magnitude and direction, at the surface of a solid boundary as a fluid flows over that boundary. The sensor is a micro-mechanical capacitor-transducer system that includes a micro-dimensioned floating upper plate above a fixed lower plate supported on a substrate. The floating upper plate is mounted and held over the substrate by a number of zig-zap form supporting arms. The flow passing over the upper plate displaces the upper plate in a downstream direction, which results in a measurable change of the capacitance in the capacitor-transducer system. The direction and magnitude of the shear forces can then be obtained from the measured capacitance through specially designed circuitry.

28 Claims, 8 Drawing Sheets

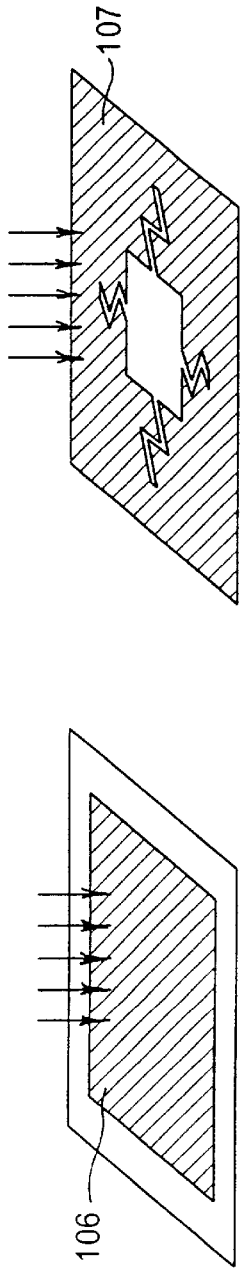
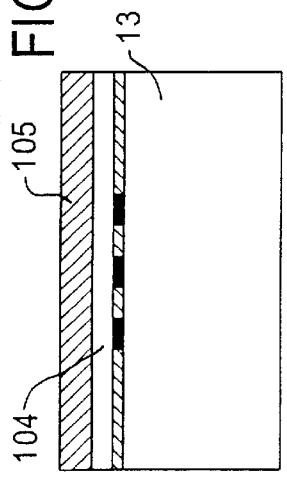
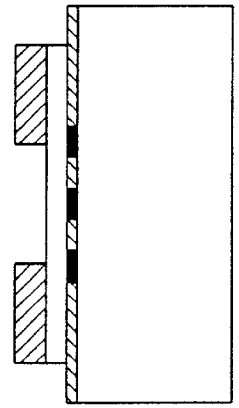
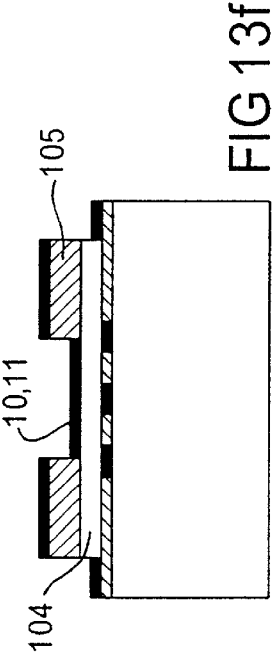
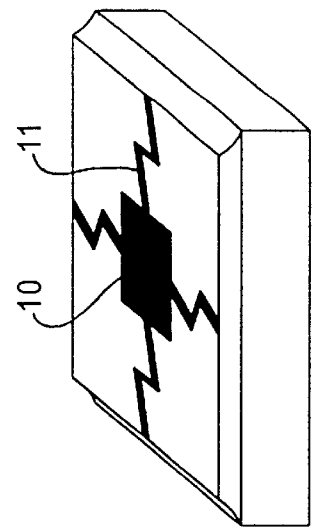
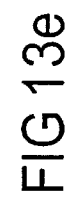
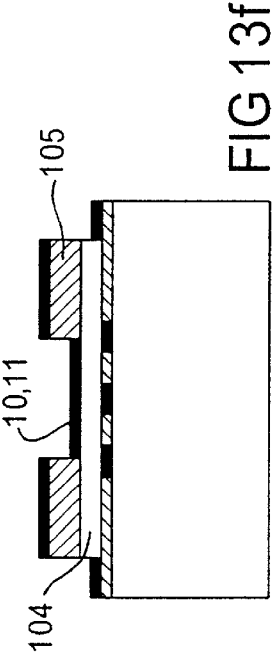

SHEAR FORCE MICROSENSOR

BACKGROUND TO THE INVENTION

Fluid flow has two fundamental characteristics. One is that there is no discontinuity of velocity; the second is that, at a solid boundary, the velocity of the fluid relative to the surface is zero. Close to the surface there is therefore a region in which the velocity increases rapidly from zero and approaches the velocity of the main fluid flow stream; this is the boundary layer. The increase in velocity with increasing distance from the solid boundary involves relative movement between the particles in the boundary layer and shear stresses here are therefore of prime importance. The fluid flow in the boundary layer immediately adjacent to the solid boundary is laminar.

The shear force on the solid boundary of an object, both in magnitude and direction, is one of the most important parameters when determining the hydrodynamic or aerodynamic performance of the object and in studying the flows around the object, especially flows near the walls of the object. The magnitude and the direction of the shear force can be used to calculate the overall drag as well as to predict the separation lines of flows on the surface of the object.

There are a number of techniques available for the measurement of shear forces in fluid flow, such as the Preston tube, hob film techniques and the direct measurement technique.

The Preston tube, a type of pressure sensing tube, is used to measure the pressure of the fluid. The pressure can be regarded as a function of the non-dimensional velocity profile, which is non-dimensioned by the inclusion of a term for the shear stress at the boundary. Therefore, the measurement of pressure is directly linked to the measurement of shear stress. Once the pressure is measured, the shear stress can be obtained indirectly according to the relationship between the two variables. This method, however, depends on the knowledge of the velocity profile which can only be known with any precision in a very limited number of cases.

Turning to hot-wire and hot-film techniques, when a high temperature object is placed in a lower temperature environment the heat will transfer from the hot object to the cold environment, the heat transfer being a nonlinear function of the temperatures of both the hot object and the cold environment, as well as the velocity profile of the fluid flow around the hot object, and a number of other thermodynamic parameters. The hot-film technique employs a thin platinum film fused to a support which is heated, and the heat loss from the hot film is measured in order to calculate the shear stress according to the relationship between the heat transfer and the velocity profile of the flows, according to a calibrated temperature-velocity profile. However, the heat transfer from the hot film often causes a change in temperature of the adjacent solid surface and the surrounding fluid, thus disturbing the flow field. As a result, the measurement and the calibration may not be accurate. Moreover, the output is nonlinear, whilst the signal-to-noise ratio is small and the frequency response poor compared to ordinary hot-wire techniques. Thus, the use of the hot-film technique is cumbersome and somewhat unreliable, and such techniques are limited in application.

Direct measurement sensors are also known. A typical such sensor is the so-called "floating element" sensor, and one such floating element sensor is disclosed in U.S. Pat. No. 4,896,098 by Haritonidis et al, issued on Jan. 23, 1990. The sensor disclosed comprises a micro-dimensioned square plate suspended above a substrate by four micro-dimensioned support arms. The micro size of the sensor substantially reduces the pressure gradient across the plate, and the sensor enables the resolving of very small fluctuations in turbulent flow fields. Furthermore, the plate is suspended at a height above the substrate which forms a very small passageway or cavity between the plate and substrate. The dimensions of the passageway are so small that vertical (ie. normal to the surface of the plate) movement of the plate by forces due to vibration is heavily suppressed by viscous damping within the passageway. The dimensions of the plate and the damping effect of the passageway enable the micro-dimensioned sensor to be substantially insensitive to vertical forces yet sensitive to shear forces acting one it. Readout means which are also substantially insensitive to vertical movement are incorporated in the sensor to provide an indication of sensed shear stress. However, the patent does not consider the measurement of the direction of the shear forces in a single measuring element, nor is the sensor able to be used to measure this direction. The direction of the shear force acting at a solid boundary is essential to describe the patterns of sheer stress and to determine the separation lines or points in laminar or turbulent fluid flows. Moreover, the sensor described in this patent is somewhat limited in its sensitivity.

Moreover, the sensor described in this prior art document is somewhat limited in its sensitivity.

SUMMARY OF THE INVENTION

The invention provides a sensor for measuring shear stress at a solid boundary in a fluid flow including a floating element arranged for resilient movement in all directions in a single plane for measuring shear stress in that plane. The element is spaced from a substrate to form a cavity therebetween. The substrate includes a two-dimensional array sensors for measuring the displacement of the element in both magnitude and direction.

The present invention therefore provides a sensor for measuring shear forces at a solid boundary which addresses the shortcomings of the prior art. In particular, the present invention provides a floating element shear force sensor which is suitable for measuring both the magnitude and direction of the shear force in a single sensor unit.

In a preferred form, the two-dimensional array includes a two-dimensional array of conductive plates provided in or on said substrate, said floating element comprising a further conductive plate, and said array of conductive plates being electrically connectable to an output to provide a measure of the displacement of said floating element in said plane.

Preferably, the floating element is suspended for movement in said plane relative to the substrate by a plurality of meandering support arms, having preferably a zig-zag form, and these support arms advantageously may have a significantly higher bending stiffness in a direction normal to said plane than in a direction in said plane. The displacement sensitivity to shear force of the device is preferably at least about 1.4 $\mu$m/Pa.

In a preferred form, the array of substrate conductive plates includes a first plate positioned centrally relative to the floating element and four outer plates substantially uniformly distributed around the periphery of and spaced from said first plate, each of said conductive plates being connectable to output circuitry to provide measures representative of the shear stress acting on said floating elements.

In one form of the invention, said floating element is constituted in its entirety by said floating further conductive plate.

The floating element may comprise a square plate, suspended by four meandering support arms in the plane of the floating element, or alternatively may comprise a circular plate, suspended by three meandering support arms.

Ideally, the floating element is sufficiently small that the pressure over the floating element is substantially uniform and the pressure gradient thereacross substantially negligible, and the cavity between the floating element and the substrate being sufficiently thin that the floating element is effectively damped against vibration, the sensor therefore being highly insensitive in a direction normal to said plane.

Preferably, the floating element has a maximum dimension of less than about 1000 microns, preferably less than about 400 microns, and the cavity is less than about 10 microns in thickness, ideally less than 2 microns.

For measuring shear stress at the solid boundary of an object in a fluid flow field, the sensor may be mounted to the object such that the surface of the floating element lies substantially flush with the surface provided by the solid boundary, and to this end the sensor may be suspended within a recess provided in the solid boundary of the object.

In a preferred form, the floating element and the conductive plates are fabricated by photolithographic micromachining techniques, which also enables constituent electrodes and solid state circuit components to be fabricated in like manner.

The sensor may sense capacitive coupling between the conductive capacitor plates as said floating element displaces and includes at least two matched field effect transistors, one transistor coupled to a first sensing node to sense change in capacitive coupling between the conductive plate of the floating element and one of the substrate conductive plates, and the other transistor coupled to a second sensing node to sense change in capacitive coupling between the conductive plate of the floating element and another one of the substrate conductive plates.

In a preferred form, the sensor includes two pairs of matched field effect transistors, each pair sensing change in capacitive coupling between the conductive plate of the floating element and two of said four outer substrate conductive plates, said first central substrate conductive plate being arranged to receive a constant AC drive signal.

In a further aspect, the invention provides a method for measuring shear stress at a solid boundary in a fluid flow including the steps of:

providing at said solid boundary a floating element arranged for resilient movement in all directions in a single plane, said element being spaced from a substrate to form a cavity therebetween, providing said substrate with a two-dimensional array providing signals representing a measure of the displacement of said floating element in said plane; and processing said signals to provide an output representing the magnitude and direction of the shear stress at said solid boundary.

In a preferred form, said floating element comprises a conductive plate and said substrate is provided with a two-dimensional array of conductive plates. The conductive plates of said substrate array are electrically connected to provide said signals representative of the capacitive coupling between the floating element conductive plate and the individual conductive plates of said substrate array.

BRIEF DESCRIPTION OF THE DRAWINGS

FIGS. 13a–g show the subsequent fabrication process of the floating element of the micro sensor;

DETAILED DESCRIPTION

When a solid object moves in a viscous fluid or viscous fluid flows around a solid object, viscous action near the surface of the object gives rise to a velocity gradient in the neighbourhood of the surface, and the solid object is therefore subject to shear forces (or shear stresses) at its surface. In laminar flow conditions shear stress is the product of the viscosity of the fluid and the velocity gradient. The integration of the shear force over the surface in the direction of fluid flow will determine the total drag on the object, which in turn determines the performance of the object in the flow field. The accurate measurement of shear stress, both in magnitude and direction, is therefore very important for application design.

Figure 1:
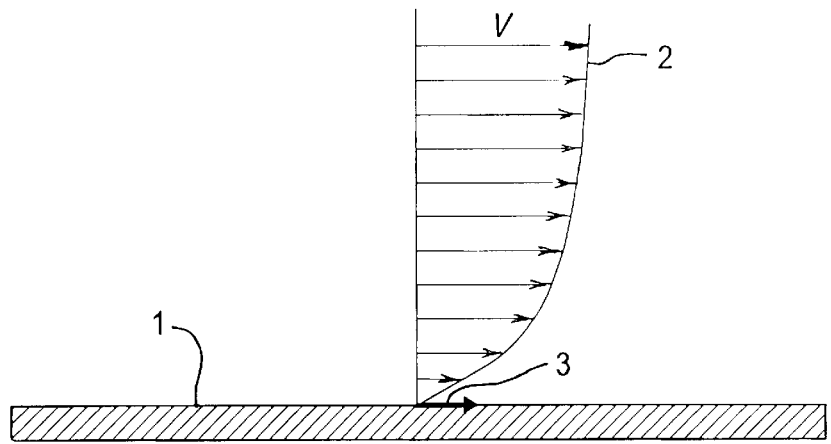
FIG. 1 is a diagrammatic representation of fluid flow over a solid boundary, which illustrates that when a viscous flow passes over a solid boundary it causes shear forces on the surface of the solid boundary.

FIG. 1 illustrates a velocity profile of a viscous flow 2 over the surface of a solid boundary 1. The gradient of velocity with respect to distance normal to the surface and the viscosity of the fluid will produce a shear force 3 at the surface, which can be expressed:

$$\vec{\tau}_w = \mu \left( \frac{\partial \vec{V}}{\partial n} \right)_w \qquad \text{Eq. 1}$$

where $\tau_w$ is the shear stress at the surface, $\mu$ is the viscosity of the fluid, V is the velocity and n is the normal distance from the surface of the solid boundary. The shear stress is a vector quantity, in the downstream direction of the fluid flow.

For a 2-dimensional incompressible laminar boundary flow over a plane plate, the shear stress can be calculated according to Blasius' solution:

$$\tau_w = \frac{0.332}{\sqrt{Re_x}} \rho V_\infty^2 \qquad \text{Eq. 2}$$

where $\tau_w$ is the shear stress, $Re_x$ the Reynolds number calculated at the distance x measured from the leading edge of the plate, $\rho$ the density and $V_\infty$ the upstream velocity. For airflow at 10 m/s with $Re_x=10^3$, $\tau_w \approx 1.26$ N/m².

The shear force, F, can be calculated as follows:

$$\vec{F} = \vec{\tau}_w A \qquad \text{Eq. 3}$$

wherein F is the shear force and A is the area of the surface over which it acts. For example, for a plane circular plate with a diameter of 400 microns, the drag will be about $1.583 \times 10^{-7}$ N, or about $2.016 \times 10^{-7}$ N in the case of a plane square plate with a side dimension of about 400 microns.

Figure 2:
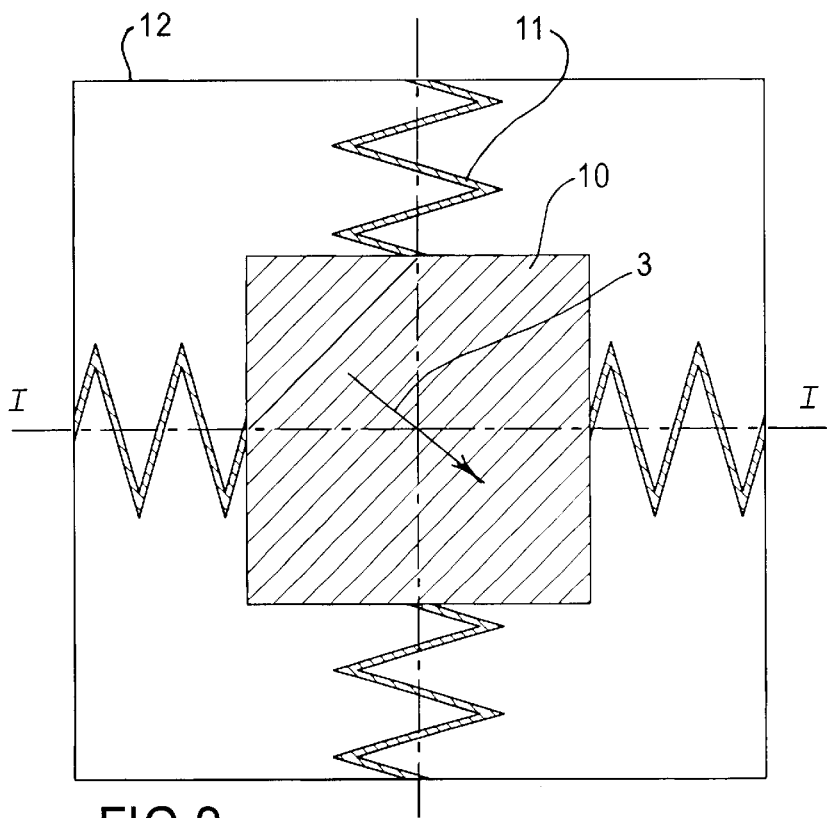
FIG. 2 is a plan view of a micromachined upper plate (or floating element) and zig-zag-form supporting arms according to the present invention.

The shear stress sensor of the invention shown in FIG. 2 includes a micromachined shear-sensitive floating sensing element 10 consisting of a square thin film plate having a side dimension of about 400 microns and a thickness of around 2 microns. Floating element 10 is supported in a holder 12 by four zig-zag support arms 11, one extending from the central position of each of the four sides as shown. The gap between floating element 10 and surrounding holder 12 permits lateral deflection of floating element 10 under the action of wall shear forces 3, and this gap is as small as practicable to limit the disturbance to the local fluid flow.

Figure 3:
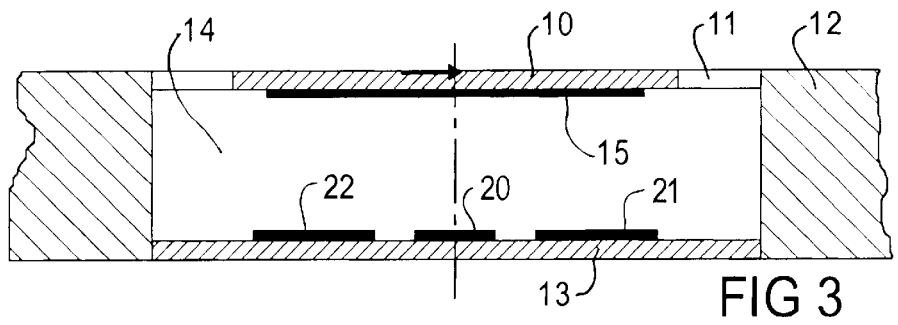
FIG. 3 is a cross section of the element of FIG. 2 through section A—A.

The cross sectional view of FIG. 3 shows sensing element 10, zig-zag arms 11, holder 12 and a lower planar substrate 13 fixed to holder 12 such that elements 10 and 13 are parallel and define a thin intermediate cavity 14 of less than 2 microns in thickness. Fluid pressure within the cavity will approximate to that across the top of floating element 10 and therefore pressure effects normal to the plane of element 10 are negligible. If fluid pressure varies laterally over the top surface of floating element 10 it will do so equally over the bottom surface. Moreover, the micro-dimensioning of cavity 14 means that viscous effects are significant and element 10 experiences viscous damping, which dampens any movement of the element normal to its surface. Non-lateral effects on the floating sensing element are therefore effectively eliminated. Similarly, the element is substantially insensitive to acoustic pressures as long as the wavelengths of acoustic pressure waves are considerably larger than any characteristic dimension of floating element 10.

FIG. 3 also depicts upper conductive capacitor plate 15 and lower conductive capacitor plates 20, 21, 22 as described in more detail below. It is to be noted that this embodiment of the invention comprises a conductive capacitor plate 15 on the lower surface of floating element 10, wherein floating element 10 may be fabricated from a non-conductive material or from a semiconductive material such as silicon. It is to be noted that conducting plate 15 does not need to be provided on the lower surface of element 10, and may alternatively be arranged embedded in or on top of the element. As explained in greater detail below, for simplicity, compactness and sensitivity, the conductive capacitor plate 15 may constitute the entirety of floating element 10, wherein floating element 10 is fabricated from a conductive material such as aluminium.

Figure 4:
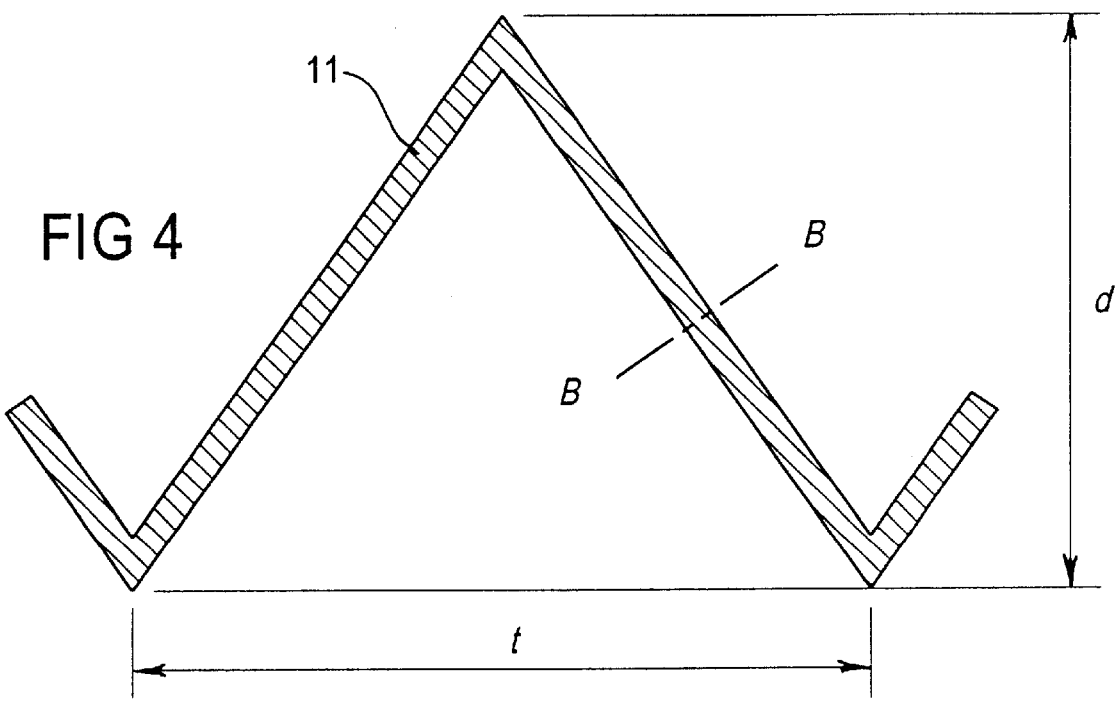
FIG. 4 is representation of one of the zig-zag support arms.
Figure 5:
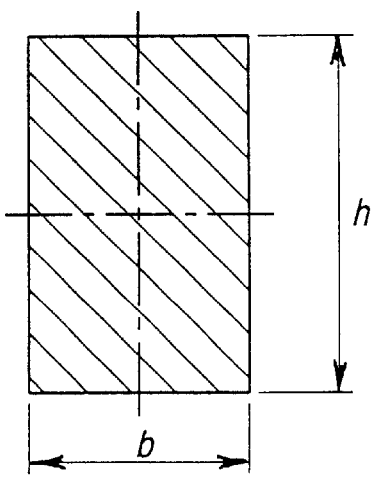
FIG. 5 shows a cross sectional view through section B—B of FIG. 4.

The sensitivity of floating sensing element 10 to shear forces 3, both in magnitude and direction, is dependent on the design of resilient support arms 11 (FIGS. 4, 5). These arms are produced with a zig-zag shape and a very fine rectangular cross-section as shown, and enable floating element 10 to be displaced laterally with relative ease in any direction, but provide a considerably greater stiffness against any displacement normal to the surface of the element.

Under a viscous shear force F, floating element 10 will be displaced by a distance $\delta_H$.

The relationship between the shear force 3 and the displacement can be represented as follows:

$$\delta_H = \frac{Ld^3 F}{\cos^2 \frac{\theta}{2} htb^3 E} \qquad \text{Eq. 4}$$

$$\cos^2 \frac{\theta}{2} = \frac{d^2}{\frac{t^2}{4} + d^2} \qquad \text{Eq. 5}$$

wherein $\delta_H$ is the horizontal displacement of floating element 10, L is the length of zig-zag arm 11, d is the overall width of the arm, F is the shear force 3 on element 10, t is the pitch of the zig-zag, h is the height of the section of the arm, b is the width of the section of the arm (see FIG. 5) and E is the elastic modulus of the arm 11.

Once the displacement $\delta_H$ has been measured, shear force F is expressed as:

$$F = \frac{\cos^2 \frac{\theta}{2} htb^3 E \delta_H}{Ld^3} \qquad \text{Eq. 6}$$

From Eq.6, for a selected material, the sensitivity of the sensor depends on the geometry of the design of the floating element 10 and the zig-zag arms 11. In the embodiment illustrated, if the parameters are selected as shown in Table 1 below:

TABLE 1.

| Dimension Parameters ($\mu$m) | | | | |
| --- | --- | --- | --- | --- |
| h | b | L | d | t |
| 2 | 1 | 300 | 50 | 30 |

Taking $E = 77.0 \times 10^9$ N/m² for aluminium, then the equation above gives $\delta_H = 1.784$ $\mu$m when the fluid velocity is 10 m/s and the size of the floating element is 400 $\mu$m × 400 $\mu$m.

In other words, the sensitivity of the sensor is 1.416 $\mu$m/Pa.

As mentioned above, the device eliminates as far as possible vertical displacement by careful selection of the geometrical parameters of the zig-zag arms. The ratio of horizontal (lateral) displacement to vertical (normal) displacement is given by:

$$\frac{\delta_H}{\delta_V} = \frac{d^3 hF}{2\cos^2\frac{\theta}{2}\sin\frac{\theta}{2}tb^2L^2\Delta p} \qquad \text{Eq. 7}$$

where $\delta_V$ is the vertical displacement (caused by any pressure gradient $\Delta p$ across floating element 10) and $\theta$ is the angle of the zig-zag, is defined as:

$$\tan\frac{\theta}{2} = \frac{t}{2d} \qquad \text{Eq. 8}$$

It can be seen from Eq.7 that, in order to increase the ratio of horizontal to vertical displacement, the overall width d of the zig-zag arms and the height h must be increased, while angle $\theta$, pitch t, sectional width b, and arm length L must be decreased. However, close attention must be paid to the length of the arm L, because it also affects the displacement of element 10.

The design of the sensing element and the electrical measuring circuitry (see below) of the invention permit the measurement of the direction of the shear force experienced by the floating sensing element 10, as well as its magnitude, by measuring the components of displacement in the x-direction and the y-direction.

Figure 6:
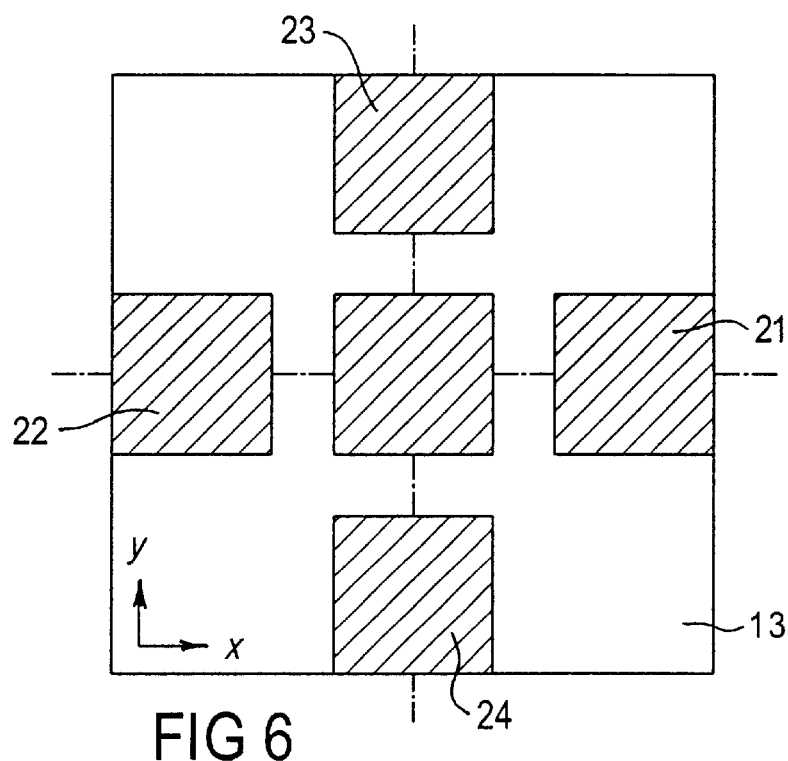
FIG. 6 is a plan view of the conductive plates of the array of the capacitance measuring circuit on the lower substrate.

As FIGS. 3 and 6 illustrate, the sensing of the displacement of floating element 10 may be realised by way of conductive capacitor plates mounted to the underside of element 10 and the upperside of substrate 13. A thin layer of conductive film is deposited on the underside of planar element 10 to provide conductive capacitor plate 15, whilst a thin layer of conductive film is also deposited on the upperside of lower substrate 13 in five discrete areas to provide conductive capacitor plates 20, 21, 22, 23 and 24. These five capacitor plates are of square shape, equally sized, with a drive capacitor plate 20 deposited centrally and the other four conductive plates 21–24 each provided aligned with and evenly spaced from each of the four sides of central drive capacitor plate 20 as shown in FIG. 6. Through the electrical circuitry described below each of the peripheral capacitor plates 21–24 on lower substrate 13 are individually coupled with drive capacitor plate 20 to form, via the intermediary of capacitor plate 15, a number of individual capacitors acting over the gap provided by microcavity 14. Clearly, displacement of floating element 10 will cause changes of the capacitance in these individual capacitors, and by measurement of the changes in the capacitances it is possible to obtain a measure of the displacement of floating element 10 and hence of the shear force 3 acting on the element, both in magnitude and direction.

As element 10 is displaced downstream by viscous shear forces the capacitance of each individual capacitor will increase or decrease differently depending on the location of the relevant conductive plate on substrate 13. Capacitance is a function of the effective area of a capacitor and the distance between the capacitor plate according to the equation:

$$C = \varepsilon\frac{A}{d} \qquad \text{Eq. 9}$$

where C is the capacitance, $\varepsilon$ is a constant (permittivity), A is the effective area of the capacitor and d is the distance between the two capacitor plates.

Displacement of floating element 10 will cause changes in the effective area of each of the individual capacitors.

For example, if shear force 3 acts to displace the floating sensor element in a direction from the upper right to the bottom left of the arrangement of FIG. 6 the effective area A of the capacitors comprising capacitor plates 22 and 24 will increase and that of the capacitors comprising plates 21 and 23 will decrease, thus proportionately changing each measured capacitance.

Figure 7:
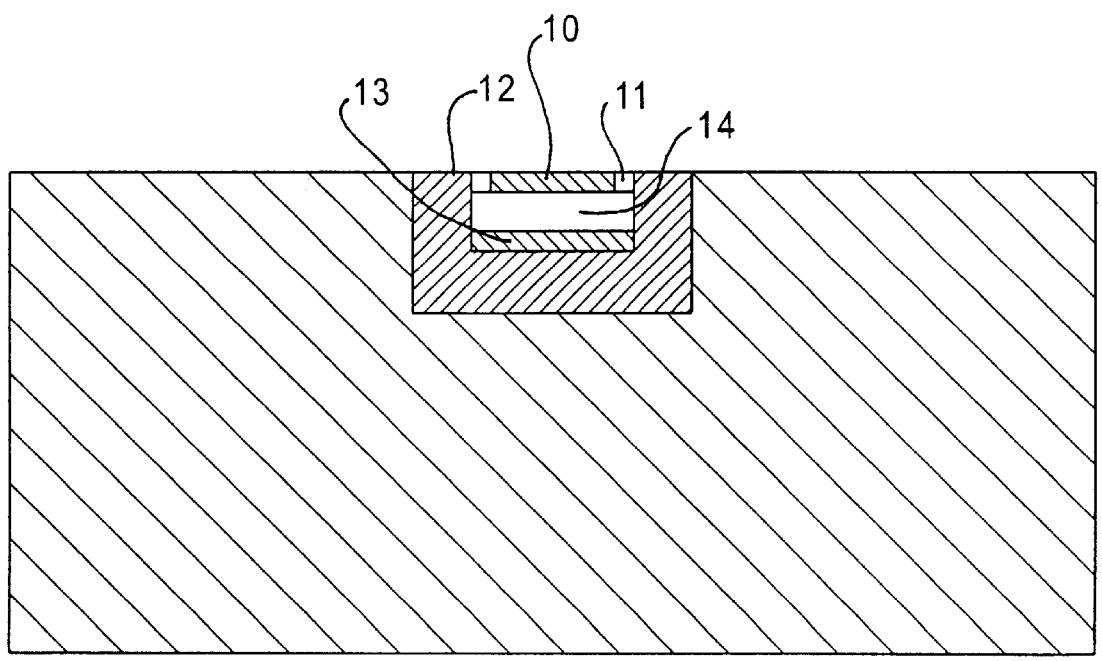
FIG. 7 schematically illustrates the overall mounting of the sensor of the invention.
Figure 8:
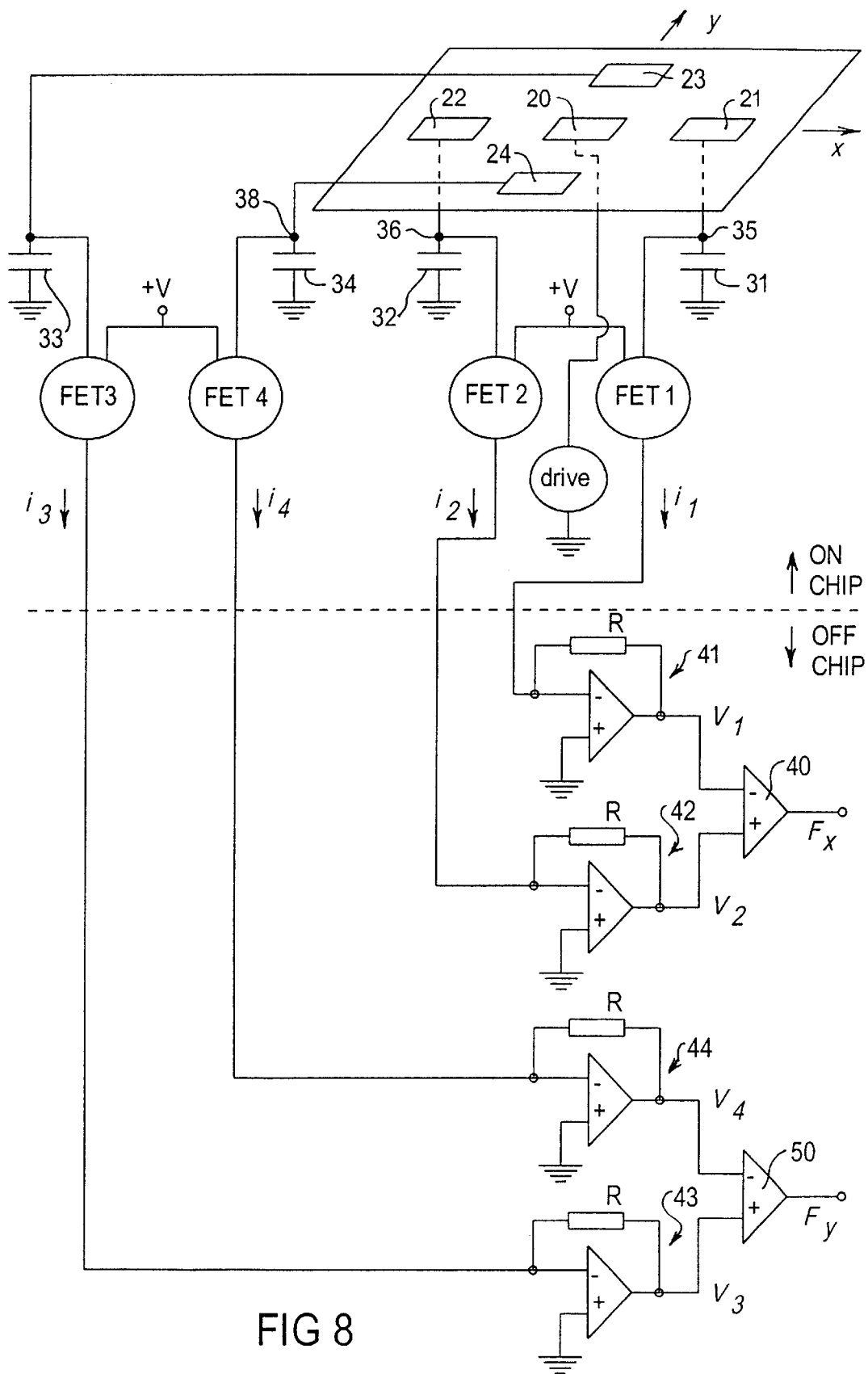
FIG. 8 shows part of an electrical circuit diagram of an integrated capacitance measuring circuit which provides a measure of the shear force at the solid boundary in two mutually orthogonal directions, $F_x$ and $F_y$.

FIG. 7 shows how the device of the invention is mounted in a cavity or recess micromachined in an object at whose solid boundary shear force is to be measured (eg in a probe head for fluid flow analysis). The upper surface of element 10 lies flush with the solid boundary as does the exposed surface of holder 12 as shown, and this is accomplished by pressing the sensor into place by means of a jig piece and adhering it there by epoxy or other adhesive means.

In FIGS. 8, 9, 10 and 11 the layout of the conductive capacitor plates and electrical circuit configuration for generating and processing the required electrical signals is illustrated. When seen in plan view, the outer edges of capacitor plate 15 on the underside of element 10 (or the outer edges of floating element 10 if the conductive capacitor plate comprises the entirety of the floating element) are aligned within the bounds of the square defined by the outer edges of sensing capacitor plates 21, 22, 23 and 24. Capacitor plates 21 and 22 make up one pair of conductors to measure the effect of shear stress in the x direction while capacitor plates 23 and 24 make up another pair to measure the effect of shear stress in the y direction. Drive capacitor plate 20 is connected to an AC generator to produce a constant amplitude AC drive signal, whilst capacitor plates 21–24 are capacitively coupled to drive capacitor plate 20 via conductive capacitor plate 15.

If the floating sensing element 10 moves laterally in the x direction, to take an example, the sideways displacement of plate 15 causes the capacitive coupling associated with one of the capacitor plates 21 and 22 to increase and the other to decrease in like amounts. This change in capacitance is sensed at nodes 35 and 36, which places a charge from their respective capacitors 31 and 32 on the gates of respective field effect transistors FET1 and FET2. The FETs are essentially identical, which is readily achieved if both are fabricated as part of the sensor using standard integrated circuit fabrication technology. In turn FET1 and FET2 change the currents $i_1$ and $i_2$ flowing to amplifier circuits 41 and 42 and provide buffered output signals $V_1$ and $V_2$. Signals $V_1$ and $V_2$ are compared through amplifier 40 and thus provide an output signal $F_x$ indicative of the sensed shear force in the x direction. Similarly, the shear force $F_y$ in the y direction can be measured by way of electrodes 23 and 24 with a second corresponding amplifier circuit (33, 34, 37, 38, FET3, FET4, 43, 44 and 50). As indicated above, the FETs, as well as the capacitors 31–34, are fabricated as part of the microfabrication of the sensor.

Figure 9:
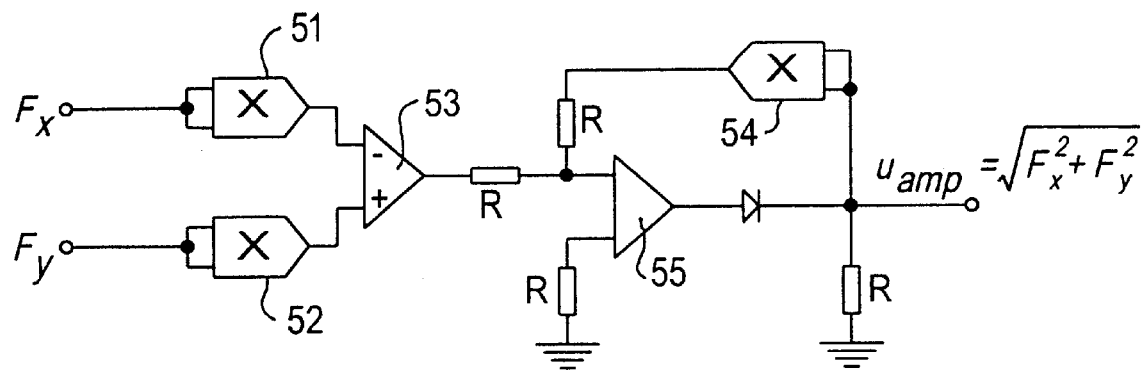
FIG. 9 shows an electrical circuit diagram which provides a measure of the amplitude of the shear force at the solid boundary.

The circuitry depicted in FIG. 9 provides an output signal representative of the amplitude of the shear force experienced by floating element 10. Orthogonal shear force signals Fx and Fy are respectively passed through squaring units 51 and 52, the squared outputs then being additively combined by way of amplifier 53 and passed through square routing circuitry including squaring unit 54 and comparator amplifier 55 as shown, to provide an output signal $$u_{amp} = \sqrt{F_x^2 + F_y^2},$$

representative of the amplitude of the shear force on the floating sensor element.

Figure 10:
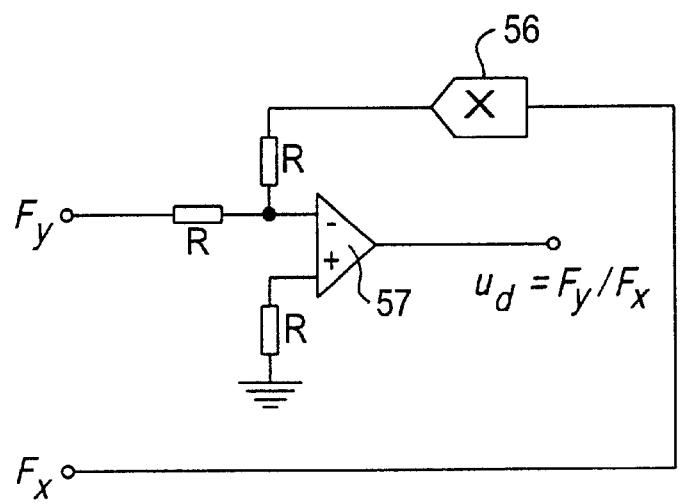
FIG. 10 shows an electrical circuit diagram which provides a measure of the tangent of the flow direction angle.

The circuitry shown in FIG. 10 is employed to provide an output signal representative of the tangent of the direction $u_d=F_y/F_x$ of the shear force experienced by element 10, ie. of the flow direction. Orthogonal shear force signals $F_x$ and $F_y$ are passed through dividing circuitry 56, 57 as shown to provide the required output signal $F_y/F_x$.

Figure 11:
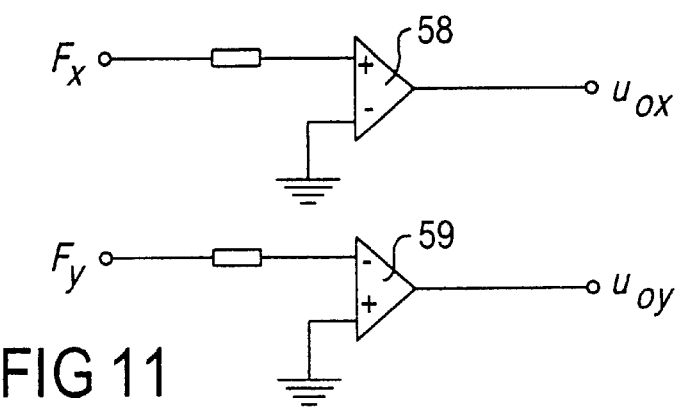
FIG. 11 shows an electrical circuit diagram which provides a measure of the shear force at the solid boundary in the x and y directions.
Figure 12A:
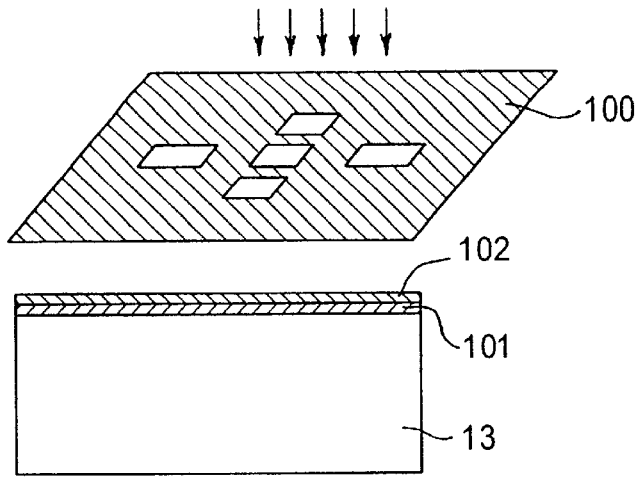
FIGS. 12a–f show the fabrication process of the lower substrate of the micro sensor of the invention.
Figure 12B:
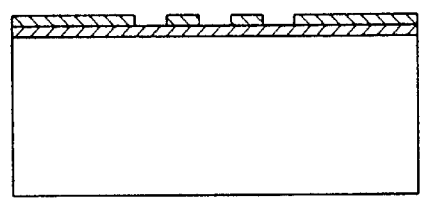
Figure 12C:
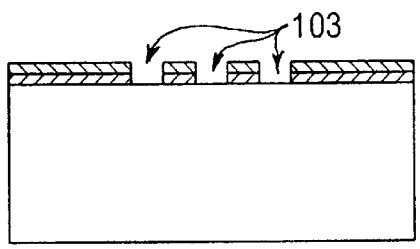
Figure 12D:
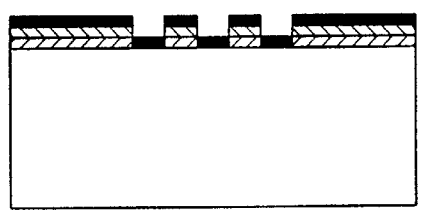
Figure 12E:
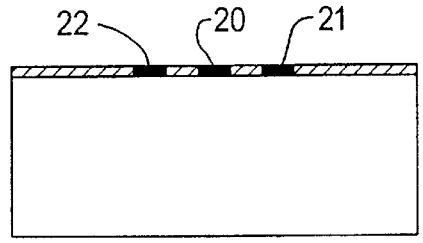
Figure 12F:
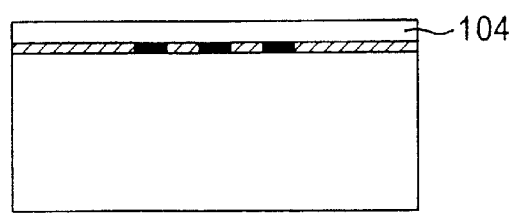

FIG. 11 shows a circuit diagram providing an output $u_{ox}$, $u_{oy}$ from input signals $F_x$, $F_y$ by way of amplifiers 58 and 59, $u_{ox}$ and $u_{oy}$ being, respectively, the sign of the shear stress $F_x$, $F_y$ at the solid boundary in the x and y directions.

As an alternative to the differential amplifier circuitry described above, the output signal from the capacitor-transducer system may be passed to a computer and all readout processing carried out by way of appropriate software.

In a preferred form, the system may include CMOS integrated detection electronics and analogue-to-digital conversion to facilitate data acquisition from the array of shear-sensitive elements.

The fabrication of the shear stress sensor is realised by means of micromachining techniques. Such techniques are well known and one method of fabrication will be described below for the production of a sensor of the form shown in FIG. 2 having a floating element comprising a conductive aluminium plate, although it is to be understood that other particular methods suitable for the production of microdimensioned elements are also within the contemplation of the present invention. The capacitor plates, associated electrodes, and integrated circuit or other readout means may be incorporated into the microfabrication process by surface micromachining. The readout means are positioned downstream from the sensing element so as not to disturb the flow before it is detected.

Both floating element 10 (and its support arms 11) as well as lower substrate 13 are monolithically fabricated from a wafer substrate by an integrated-circuit technique, namely by employing photolithographic etching to form a desired structure on a suitable substrate (such as silicon), and FIG. 12 represents the process employed for fabricating lower substrate 13. Silicon dioxide layer 101 is grown on the surface of substrate 13 by reaction with steam at 1200° C. and, by a standard photolithography technique, a photo resist layer 102 is etched using a mask 100 (FIG. 12a) laid over substrate 13, to structure resist layer 102. The developed resist layer (see FIG. 12b) represents an inverse projection of the desired electrode configuration. The silicon dioxide layer is then etched using hydrofluoric acid (FIG. 12c) to remove the silicon dioxide in selected areas 103 (ie those areas not coated with the resist), after which metal deposition (eg. by standard CVD) or diffusion takes plate (FIG. 12d) filling the recesses 103 and providing a conducting coating to substrate 13 in the desired conductive plate configuration. Finally the mask is removed by a lift-off technique using a suitable solvent (FIG. 12e), and a 2 $\mu$m sacrificial layer 104 (eg of silicon dioxide) deposited (FIG. 12f).

Turning to FIG. 13 (fabrication of floating conductive element 10), a photo resist layer 105 of 3 $\mu$m is deposited on the surface of sacrificial layer 104, and then selectively photolithographically etched through a mask 106 as shown in FIG. 13b, after which reactive ion etching (RIE) is applied to remove unwanted sacrificial layer 104 (FIG. 13c). Further selective photolithographic etching through a further mask 107 (FIG. 13d) is then carried out to produce a structure (FIG. 13e) on which metal deposition (2 $\mu$m) or diffusion then takes place to provide upper floating sensor element 10 and support arms 11 (FIG. 13f). Finally a lift-off technique is applied to remove photo resist layer 105 and unwanted metal deposit, and sacrificial layer 104 is removed by a selective etchant to leave the floating sensor element 10 suspended over the lower substrate by support arms 11 (see FIG. 13g). The removed sacrificial layer defines the microcavity 14 between the lower capacitor plates 20–24 and the upper element 10.

Figure 14:
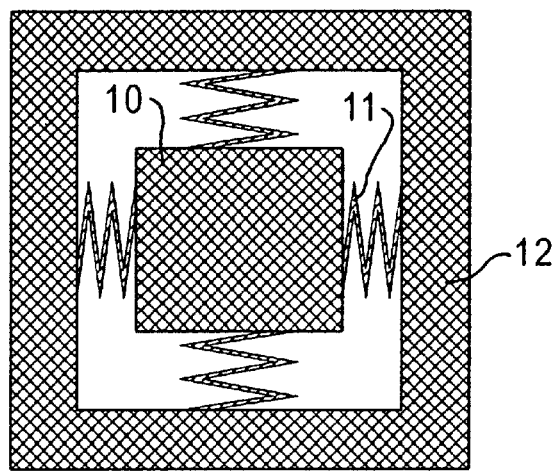
FIG. 14 is a plan view of the floating element of the micro sensor.

Lithography mask 107 is an inverse projection of the desired element/arm configuration used to shape the resist 105 into the desired form as diagrammatically depicted in plan view in FIG. 14.

Figure 15:
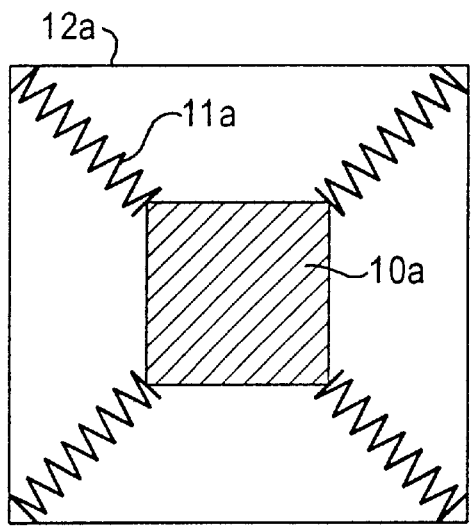
FIG. 15 is a plan view of a sensor floating element according to an alternative embodiment of the invention.

A further possible floating sensor arrangement is shown in FIG. 15, in which the four meandering arms 11a extend instead from the four corners of square floating element 10a, allowing longer support arms and so improved sensitivity of the device.

Figure 16:
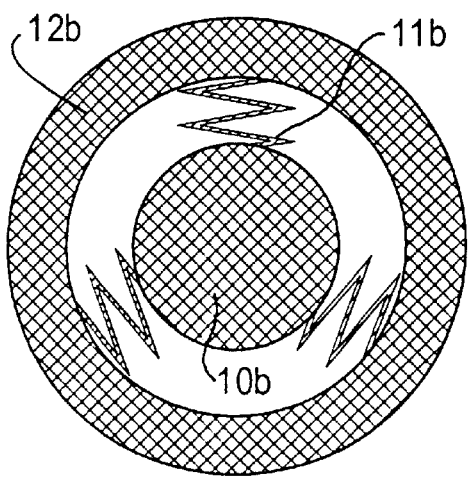
FIG. 16 is a plan view of a sensor floating element according to yet another embodiment of the invention.

FIG. 16 shows an alternative form of floating sensor having a circular upper plate 10b suspended within an annular gap from a surrounding holder 12b as shown by way of three zig-zag support arms 11b with equal angular separations.

Such an arrangement can potentially be utilised to have an even higher sensitivity to shear forces than the square form embodiment with four support arms, and can also be used to provide a measurement of rotational forces acting on the sensor.

It is to be noted that the microdimensions of the sensor of the invention permit very high spatial resolution of the shear stress in a flow field enabling accurate analysis of shear force parameters in both laminar and turbulent flow situations. A number of such sensors may be employed in one probe head if required, to enable spatial analysis of flow characteristics.

The invention has been described in detail above with reference to a shear-sensitive array of conductive plates used to provide a measure of the displacement of the floating element, and such a system represents the inventors' preferred form of the device. However, it is to be understood that other ways of putting the present invention into effect are also contemplated within the scope of the invention. One alternative form involves the use of optical readout devices, such as those described in U.S. Pat. No. 4,896,098 referred to above, and the content of this patent is incorporated herein by reference.

It is understood that various modifications, alterations and/or additions may made to the embodiments specifically described and illustrated herein without departing from the spirit and scope of the invention.

What is claimed is:

1. A sensor for measuring shear stress at a solid boundary in a fluid flow, including:
   a floating element being suspended by a plurality of support arms for resilient movement in all directions in a single plane for measuring shear stress in that plane, said element being spaced from a substrate to form a cavity therebetween, the substrate comprising a two-dimensional array of sensors for measuring the displacement of said element in both magnitude and direction,
   the measured displacement providing an indication of the magnitude and direction of shear stress in the plane.

2. A sensor according to claim 1, wherein the two-dimensional array of sensors comprises a two-dimensional array of conductive plates provided in or on said substrate, said floating element comprising a further conductive plate, and said array of conductive plates being electrically connectable to an output to provide a measure of the displacement of said floating element in said plane.

3. A sensor according to claim 1, wherein the plurality of support arms are meandering support arms.

4. A sensor according to claim 3, said support arms having a significantly higher bending stiffness in a direction normal to said plane than in a direction in said plane.

5. A sensor according to claim 1 having a displacement sensitivity to shear force of at least about 1.4 $\mu$m/Pa.

6. A sensor according to claim 1 having associated circuitry to provide output measures representative of both the magnitude and the direction of the shear stress acting on said floating element.

7. A sensor according to claim 2, wherein the array of substrate conductive plates includes a first plate positioned centrally relative to the floating element and four outer plates substantially uniformly distributed around the periphery of and spaced from said first plate, each of said conductive plates being connectable to output circuitry.

8. A sensor according to claim 7, wherein the conductive plate of the floating element when viewed in projection on said substrate lies wholly within an area bordered by the extrapolation of the outer edges of said four outer plates.

9. A sensor according to claim 2, wherein said floating element is constituted in its entirety by said further conductive plate.

10. A sensor according to claim 1, the floating element being a square plate, suspended by four meandering support arms in the plane of the floating element.

11. A sensor according to claim 10, the support arms extending outwardly from a position approximately central to each of the four sides of the floating element.

12. A sensor according to claim 10, the support arms extending outwardly from the corners of the floating element.

13. A sensor according to claim 1, the floating element being a circular plate, suspended by three meandering support arms.

14. A sensor according to claim 1, the floating element being sufficiently small that the pressure over the floating element is substantially uniform and the pressure gradient thereacross substantially negligible, and the cavity between the floating element and the substrate being sufficiently thin that the floating element is effectively damped against vibration, the sensor therefore being highly insensitive in a direction normal to said plane.

15. A sensor according to claim 1, the floating element having a maximum dimension of less than about 1000 microns, and the cavity being less than 10 microns in thickness.

16. A sensor according to claim 15, the floating element having a maximum dimension of less than about 400 microns, and the cavity being less than 2 microns in thickness.

17. A sensor according to claim 1 in combination with an object having a solid boundary, the sensor mounted to said object such that the surface of the floating element lies substantially flush with the surface provided by said solid boundary.

18. A sensor according to claim 17, the sensor being suspended within a recess provided in the solid boundary of the object.

19. A sensor according to claim 1, the floating element and the conductive plates being fabricated by photolithographic micromachining techniques.

20. A sensor according to claim 1, including circuitry for sensing capacitive coupling between the conductive capacitor plates as said floating element displaces, said circuitry including at least two matched field effect transistors, one transistor coupled to a first sensing node to sense change in capacitive coupling between the conductive plate of the floating element and one of the substrate conductive plates, and the other transistor coupled to a second sensing node to sense change in capacitive coupling between the conductive plate of the floating element and another one of the substrate conductive plates.

21. A sensor according to claim 20, including two pairs of matched field effect transistors, each pair sensing change in capacitive coupling between the conductive plate of the floating element and two of said four outer substrate conductive plates, said first central substrate conductive plate being arranged to receive a constant AC drive signal.

22. A method for measuring shear stress at a solid boundary in a fluid flow, said method including the steps of:

providing at said solid boundary a floating element arranged for resilient movement in all directions in a single plane, said element being spaced form a substrate to form a cavity therebetween, providing said substrate with a two-dimensional array for circuitry for providing signals representing a measure of the displacement of said floating element in said plane; and processing said signals to provide an output representing the magnitude and direction of the shear stress at said solid boundary.

23. A method for measuring shear stress at a solid boundary in a fluid flow according to claim 22, wherein said floating element comprising a conductive plate and said substrate is provided with a two-dimensional array of conductive plates, including the step of:

electrically connecting the conductive plates of said substrate array to processing circuitry to provide said signals representative of the capacitive coupling between the floating element conductive plate and the individual conductive plates of said substrate array.

24. The sensor according to claim 1, wherein the supporting arms are zig-zag shaped.

25. The sensor according to claim 1, wherein the plurality of support arms are arranged radially.

26. The method in claim 22, further comprising:

supporting said element using a plurality of radially arranged support arms.

27. The method in claim 25, wherein the support arms are meandering.

28. The method in claim 25, wherein the support arms are zig-zag shaped.

* * * * *